US006551532B1

(12) United States Patent
Boissier et al.

(10) Patent No.: US 6,551,532 B1
(45) Date of Patent: Apr. 22, 2003

(54) METHOD AND DEVICE FOR FORMING PARTICLES

(75) Inventors: Catherine Boissier, Gothenburg (SE); Håkan Glad, Åsa (SE)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/600,068

(22) PCT Filed: May 4, 2000

(86) PCT No.: PCT/SE00/00877
§ 371 (c)(1),
(2), (4) Date: Jul. 10, 2000

(87) PCT Pub. No.: WO00/67892
PCT Pub. Date: Nov. 16, 2000

(30) Foreign Application Priority Data

May 7, 1999 (SE) .............................................. 9901667

(51) Int. Cl.[7] .................................................. B29B 9/10
(52) U.S. Cl. .............................. 264/5; 264/12; 264/13; 425/6; 425/7
(58) Field of Search ................................ 264/5, 11, 12, 264/13; 425/6, 7

(56) References Cited

U.S. PATENT DOCUMENTS

| | | | | | |
|---|---|---|---|---|---|
| 4,179,222 A | | 12/1979 | Strom et al. | ................ | 366/337 |
| 4,368,100 A | | 1/1983 | Pyves et al. | | |
| 4,606,939 A | * | 8/1986 | Frank et al. | ............. | 252/363.5 |
| 4,606,940 A | | 8/1986 | Frank et al. | ................ | 427/213 |
| 5,178,325 A | | 1/1993 | Nielsen | ......................... | 239/1 |
| 5,891,471 A | * | 4/1999 | Miller et al. | ................ | 424/458 |
| 5,910,321 A | * | 6/1999 | Wong et al. | ................ | 424/464 |
| 6,342,250 B1 | * | 1/2002 | Masters | ...................... | 424/443 |

FOREIGN PATENT DOCUMENTS

| | | | |
|---|---|---|---|
| EP | 0300964 | | 1/1989 |
| EP | 0322687 | | 7/1989 |
| EP | 0437451 | | 7/1991 |
| GB | 1474112 | | 5/1977 |
| WO | 8905196 | | 6/1989 |
| WO | 9600610 | | 1/1996 |
| WO | 9731691 | | 9/1997 |
| WO | 9836825 | | 8/1998 |
| WO | WO 98/53798 | * | 12/1998 |

* cited by examiner

*Primary Examiner*—Mary Lynn Theisen
(74) *Attorney, Agent, or Firm*—White & Case LLP

(57) ABSTRACT

The present invention relates to a method for forming particles of a substance, comprising the step of introducing into a mixing chamber (8), in which the temperature and pressure are controlled, a fluid gas (4) and at least one vehicle system (1) comprising at least one substance in solution or suspension such that droplet formation and extraction of the vehicle occur substantially simultaneously by the action of the fluid gas (4). Turbulence is induced in at least one of said fluid gas (4) and said vehicle system (1) so as to create a controlled disorder in the flow of the at least one of the fluid gas (4) or the vehicle system (1) in order to control the particle formation in said mixing chamber (8), said controlled disorder being created by at least one flow perturbation means (11). The invention also relates to a mixing chamber having at least one flow perturbation means (11) that is disposed for interacting with at least one of a fluid gas (4) or vehicle system (1) supplied by the at least one supply member (4, 5) so as to induce turbulence or limited disorder in the at least one of the fluid gas (4) or vehicle system (1).

19 Claims, 9 Drawing Sheets

FELODIPINE

PRIOR ART   Fig. 9a

FELODIPINE

CANDESARTAN CILEXETIL

CANDESARTAN CILEXETIL

METHOD AND DEVICE FOR FORMING PARTICLES

This invention relates to a method for forming particles of a substance. It also relates to a mixing chamber for use in forming particles of a substance.

BACKGROUND ART

The use of supercritical fluids in particle forming processes has been described in several documents. A supercritical fluid can be defined as a fluid at or above its critical pressure and critical temperature simultaneously. Such fluids are interesting in particle formation since their solving power of different substances undergoes large changes as a result of changes in the physical characteristics of the surroundings, which characteristics can be relatively easily controlled, such as pressure. This property make supercritical fluid a medium highly appreciated for having a solving power being controllable by pressure and temperature changes, which is particularly useful in extraction and atomization of different substances, such as substances used in pharmacy. Further, supercritical fluids are normally gases under ambient condition, which eliminates the evaporation step needed in conventional liquid extraction.

There are several techniques related to this phenomenon used today, one of which is known as rapid expansion of supercritical solutions (RESS) and another that is known as gas anti-solvent precipitation (GAS). In the GAS technique a substance of interest is dissolved in a conventional solvent, a supercritical fluid such as carbon dioxide is introduced into the solution, leading to a rapid expansion of the volume of the solution. As a result, the solvent power decreases dramatically over a short period of time, triggering the precipitation of particles. Documents referring to this are for example J. W Tom and P. G. Debenedetti in J. Aerosol SCI., 22 (1991), 555–584; P. G. Debenedetti et al in J. Controlled Release, 24(1993), 27–44 and J. W. Tom et al in ACS Symp Ser 514 (1993) 238–257; EP 437 451 and EP 322 687.

A modification of the GAS system has recently been developed, which is called the SEDS (solution enhanced dispersion by supercritical fluid) process, which utilises supercritical fluid technologies for particle formation.

This technique is described in WO95/01221, which reveals a method for the formation of a particulate product, which comprises the co-introduction of a supercritical fluid and a vehicle system comprising at least one substance in solution or suspension into a particle formation vessel. The temperature and pressure inside the particle formation vessel are controlled, such that dispersion and extraction of the vehicle occur substantially simultaneously by the action of the supercritical fluid.

The method described in the aforementioned document is particularly developed for use in Gas Anti Solvent (GAS) techniques. These techniques are useful in situations where the solid of interest does not dissolve in, or has very low solubility in a supercritical fluid. The solute is therefore in a first step dissolved in a conventional solvent. The solution of the solvent and the substance is commonly known under the term "vehicle system". The term "vehicle" is herein a fluid, which dissolves a solid or solids to form a solution, or which forms a suspension of a solid or solids, which do not dissolve or have a low solubility in the fluid. The vehicle can be composed of one or more fluids.

In a second step of the procedure, the vehicle is extracted by the supercritical fluid, which has a sufficient solubility for the vehicle in concern when held in a supercritical condition. As a result, extraction and droplet formation of the vehicle occurs substantially simultaneously by the action of the supercritical fluid. The particles thus formed by the substance previously carried in the vehicle system are collected in a particle vessel and the remaining supercritical fluid and vehicle products can optionally be brought through a cleaning system for possible reuse. The term "particle" as used herein can include products in a single-component or multi-component, as mixtures of one component in a matrix of another form.

In the description of the method described above, the importance of maintaining control over the working conditions, especially the pressure is set out. It is thus necessary to eliminate any uncontrolled pressure fluctuation across the particle formation vessel and ensure a uniform dispersion of the vehicle. Through a high degree of control of parameters such as temperature, pressure and flow rate of both vehicle system and supercritical fluid and the simultaneous co-introduction of the vehicle system and the supercritical fluid into the particle formation vessel, droplet formation occurs when the fluids come into contact with one another.

In the document WO95/01221 is further an apparatus for performing the method described. The apparatus is provided with means for co-introduction of the vehicle system and the supercritical fluid into the particle formation vessel. This means consists of a nozzle, having coaxial passages serving to carry the flow of the vehicle system and of the supercritical flow, respectively. The outlet end of the particle formation chamber is conical, with an angle of taper typically in the range of 10 to 50 degrees. The document teaches further that an increase in the angle may be used for increasing the velocity of the super-critical fluid introduced to the nozzle and hence the amount of physical contact between the supercritical fluid and the vehicle system. It is further imposed that control of parameters such as size and shape in the resulting particulate product will be dependent upon variables including the flow rates of the supercritical fluid and/or the vehicle system comprising the substance, the concentration of the substance in the vehicle system, and the temperature and pressure inside the particle formation vessel.

In another patent document, WO96/00610, the method is improved by introducing a second vehicle, which is both substantially miscible with the first vehicle and substantially soluble in the supercritical fluid. The corresponding apparatus is consequently provided with at least three coaxial passages. These passages terminate adjacent or substantially adjacent to one another at the outlet end of the nozzle, which end is communicating with a particle formation vessel. In one embodiment of the nozzle the outlet of at least one of the inner nozzle passages is located a small distance upstream (in use) of the outlet of one of its surrounding passages. This allows a degree of mixing to occur within the nozzle between the solution or suspension, that is the first vehicle system, and the second vehicle. This pre-mixing of the solution and the second vehicle does not involve the supercritical fluid. It is in fact believed that the high velocity supercritical fluid emerging from the outer passage of the nozzle causes the fluids from the inner passages to be broken up into fluid elements. From these fluid elements the vehicles are extracted by the supercritical fluid, which results in the formation of particles of the solid previously solved in the first vehicle. The useful maximal taper of the conical end is in this document also augmented up to 60 degrees.

Another technique for particle precipitation using near-critical and supercritical antisolvents has later been described in WO97/31691. This document mentions the use of specialized nozzles for creating extremely fine droplet sprays of the fluid dispersions. The method involves passing the fluid dispersion through a first passageway and a first passageway outlet into a precipitation zone, which contains an antisolvent in a near- or supercritical condition. Simultaneously an energizing gas stream is passed along and through a second passageway outlet proximal to the first fluid dispersion outlet. The passage of the energizing gas stream generates high frequency waves of the energizing gas adjacent to the first passageway outlet in order to break up the fluid dispersion into small droplets.

The disclosed prior art of producing small particles by use of supercritical fluid as an antisolvent to release a desired substance from a solution or suspension, do all try to achieve control over parameters such as pressure and temperature, in order to control the morphology, size and size distribution of the particles formed of the substance concerned.

The requests from for example the pharmaceutical industry for production of small particles with a narrow size distribution and a specialized morphology do however invoke the need for even better particle formation techniques than those mentioned in the disclosed prior art. New substances with new behavior in particle formation do also require new and improved methods for controlling and industrially accomplishing the particularization needed. The aim of this invention is to provide a method and a mixing chamber for production of small particles with a narrow size-distribution and uniform morphology.

SUMMARY OF THE INVENTION

The present invention relates to a method for forming particles of a substance, comprising the step of introducing into a mixing chamber, in which the temperature and pressure are controlled, a fluid gas and at least one vehicle system comprising at least one substance in solution or suspension such that droplet formation and extraction of the vehicle occur substantially simultaneously by the action of the fluid gas; wherein turbulence is induced in at least one of said fluid gas and said vehicle system so as to create a controlled disorder in the flow of the at least one of the fluid gas or the vehicle system in order to control the particle formation in said mixing chamber, said controlled disorder being created by at least one flow perturbation means.

Herein, the definition to a "fluid gas" includes material in its supercritical and near-supercritical state as well as compressed gases. The fluid gas can be, but is not limited to, carbon dioxide, nitrous oxide, sulphur hexafluoride, xenon, ethane, ethylene, propane, chlorotrifluoromethane, and trifluoromethane. For example, the lower temperature limit for a near super-critical state is for carbon dioxide $0.65 \times Tc$ and for propane $0.30 \times Tc$, where Tc is the critical temperature for the specific substance.

When deliberately creating turbulence or a disorder in the flow of fluid gas or vehicle system one differs remarkably from prior art of the area. Turbulence is known to be an extremely sensitive condition, in which the local pressures are difficult to describe in detail even in the case of ideal, incompressible gases. Using turbulence in combination with fluid gas, whose properties are known to alter dramatically with changing conditions such as pressure, one could expect a chaotic state lacking the control needed for creating small and homogeneous particles. However, it has now been shown that creation of turbulence in the fluid gas or the vehicle system before introduction into the particle formation chamber has a remarkable and stable effect on particle size and distribution.

Preferably, the turbulence is controlled so as to form the desired particles of the at least one, specific substance. The turbulence does probably need to be adjusted to different substances and vehicles so as to create particles with the properties wanted.

The controlled disorder can advantageously be created by the interaction of at least one of said fluids with the interior of the mixing chamber. The design of the mixing chamber should then be adapted to create a controlled disorder in at least one of the fluids, when said fluid encounters the interior of the mixing chamber.

Preferably, turbulence in at least one of said fluid gas and said vehicle system is occurring in a region near or adjacent to an outlet orifice of said mixing chamber, where nucleation is believed to occur. The effect on the created particles seems to be related to the altered crystallization environment that is established when at least one of the fluid flows is somewhat disturbed. It might also increase intermixing of the different fluids and hence the overall surfaces available for reaction between fluids.

The invention also relates to a particle formation chamber or mixing chamber according to the preamble and wherein at least one flow perturbation means is disposed for interacting with at least one of the fluid gas or vehicle system supplied by the at least one supply member so as to induce turbulence in the at least one of the fluid gas or vehicle system for creating a controlled disorder in the flow of the at least one of the fluid gas or the vehicle system in order to control the particle formation in said mixing chamber. The flow perturbation device is meant to constitute an obstacle for the flow in the passage of either of the fluids, and thus create the turbulence required, which in turn will affect the physical properties of the particles formed in the particle formation chamber.

Advantageously, said flow perturbation means is designed so as to induce a turbulence that is controlled so as to form the desired particles of the at least one, specific substance. Different substances with varying properties appear to need different kinds and amounts of turbulence in order to optimize the particle formation.

The flow perturbation means can be formed in the interior of the mixing chamber. The fluids entering the mixing chamber will thus encounter the perturbation means inside of the mixing chamber.

Preferably, the flow perturbation means are disposed so as to create turbulence in at least one of said supercritical fluid and said vehicle system, in a region near or adjacent to said outlet part of said mixing chamber, where nucleation is believed to occur.

Preferably, the flow perturbation means consists of a projecting member in the interior of the chamber. Such a member will constitute an effective obstacle for the flow, and thus create turbulence.

Advantageously, said flow perturbation means are constituted by at least one shelf in the wall of the mixing chamber, said shelf opposing the direction of said flow, when in use. Such a shelf will efficiently return the kinetic energy of the flow in a back-flow direction thus creating turbulence in the area around said shelf.

Preferably, the flow perturbation means is constituted by at least two separate members. Such members can be two shelves in the wall of the mixing chamber or one shelf and at least one baffle extending from said mixing chamber wall. The choice of flow perturbation means is preferably adapted to the substance of which particles are to be formed.

Preferably, the mixing chamber can comprise first and second body parts, which are detachably coupled to each other.

Manufacturing the mixing chamber in two separate parts provides the advantage of easy cleaning of the mixing chamber. In prior art, there is often a problem with particles clogging in the mixing chamber, and shutting the outlet orifice of the mixing chamber. When a two-piece mixing chamber is used, such particles can be easily removed by simply opening and cleaning the mixing chamber.

BRIEF DESCRIPTION OF DRAWINGS

Preferred embodiments of the present invention will now be described hereinafter by way of example only with reference to the accompanying drawings, in which:

FIG. 9*a* is a SEM-graph from an experiment using a prior art mixing chamber and felodipine as the particle forming substance.

FIG. 10*a* is the same as FIG. 9*a*.

FIG. 12*a* is the same as FIG. 11*a*.

DETAILED DESCRIPTION OF PREFERRED EMBODIMENTS OF THE INVENTION

Embodiments of the invention will hereinafter be described, as illustrating and non-limiting examples only.

Figure 1:
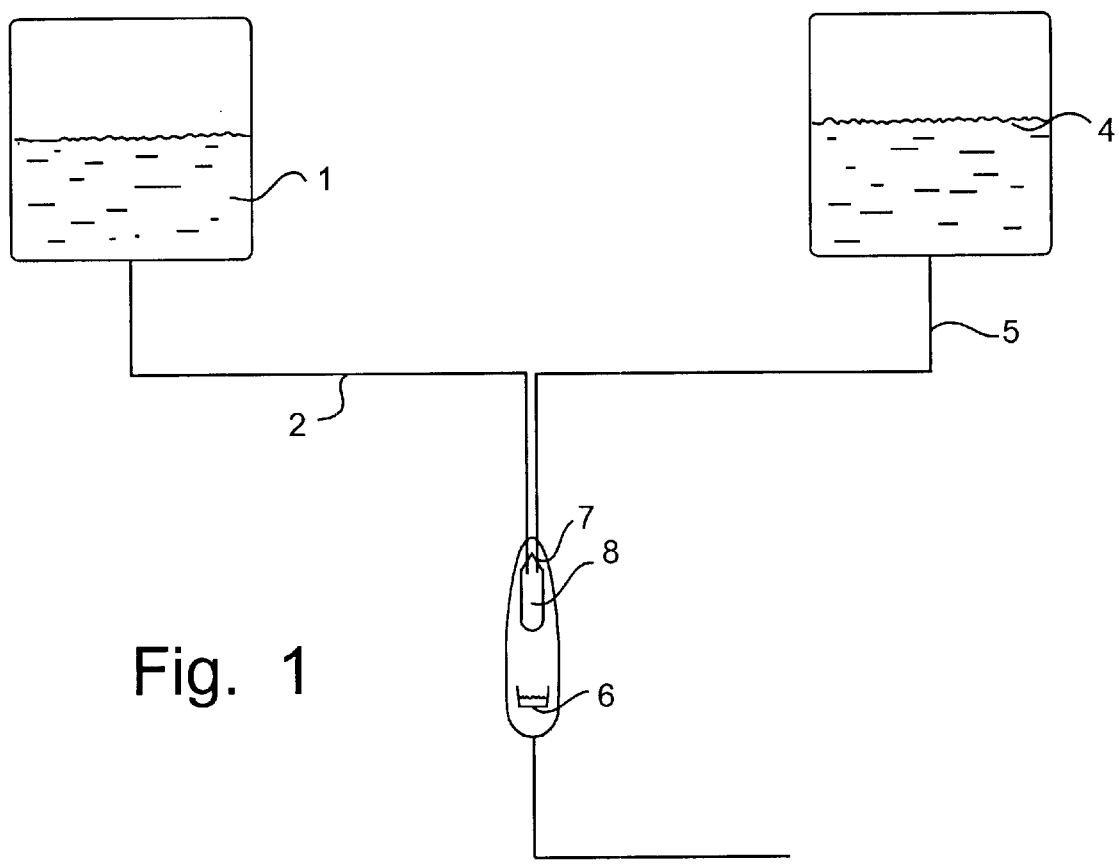
FIG. 1 shows schematically a particle production system according to prior art.

In FIG. 1 a schematic system for particle production is shown as known from prior art. A vehicle system 1, consisting of a solution or suspension containing a substance of which particles is to be formed, is introduced through a nozzle 7 to a mixing chamber or particle formation chamber 8 through a first passage 2. An antisolvent 4 in form of a fluid gas is co-introduced to the mixing chamber 8 through the nozzle 7 by a second passage 5. The mixing chamber 8 is located in an oven and has an orifice opening to a vessel 6 for collecting the particles formed by the method according to the invention. In use, the antisolvent 4 extracts the vehicle from the vehicle system 1 when intermixing under controlled temperature and pressure conditions, in which the antisolvent 4 is in a fluid gas state, inside the mixing chamber 8. When the conditions in the mixing chamber 8 are changed, the vehicle is extracted by the antisolvent 4, leading to rapid particle formation of said substance carried in the vehicle system 1. The particles are collected in the vessel 6 while the antisolvent 4 and the extracted solvent emerge through a back-pressure regulator. The nozzle 7 in this kind of apparatus could be a two- or a three-component nozzle 7 according to prior art.

Figure 2:
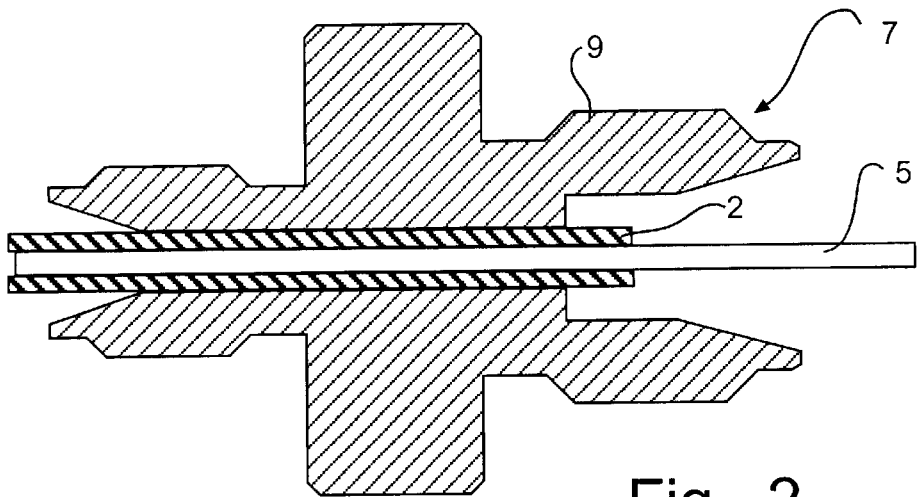
FIG. 2 is a section of an embodiment of a nozzle used together with the present invention.

The nozzle means 7 could be formed according to prior art as in FIG. 2, with a first passage 2 for the solution or vehicle system 1 and a second passage 5 for the antisolvent 4, being coaxially arranged, for substantially simultaneous introduction of the fluids 1, 4 to the mixing chamber 8. As illustrated in the example in FIG. 2, the central second passage 5 could be arranged to extend further into the mixing chamber 8 than the surrounding first passage 2. The nozzle means 7 also consists of a connector portion 9 for attachment to the mixing chamber 8.

Figure 3:
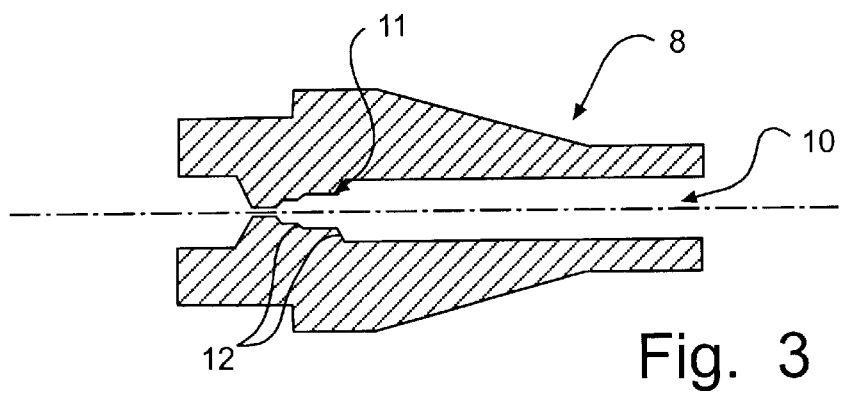
FIG. 3 is a section of an embodiment of a mixing chamber according to the invention.

FIG. 3 shows a mixing chamber 8 according to one preferred embodiment of the invention. The external shape of the mixing chamber 8 is simply adapted to be received by the connector portion 9 of the nozzle means 7. The mixing chamber 8 is correspondingly provided with a bore 10 for receiving the first 5 and the second passage 2. According to the invention, the mixing chamber 8 is also provided with flow perturbation means 11 for, when in use, disturbing the fluid flows from the first 5 and the second passage 2. In this embodiment, two chamfered shelves 12 in the wall of the mixing chamber 8 constitute the flow perturbation means 11.

Figure 4:
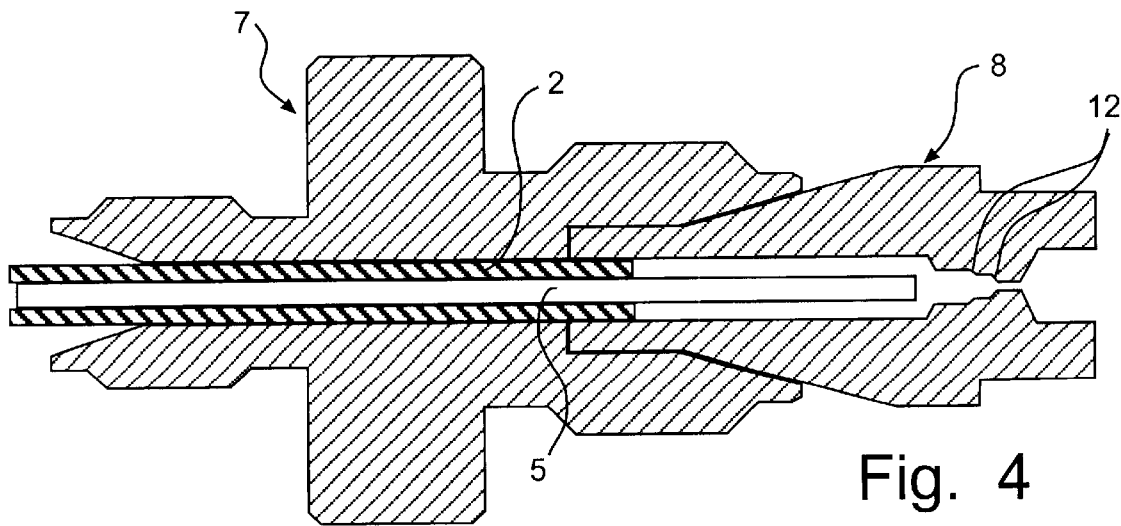
FIG. 4 is a section of the mixing chamber in FIG. 3 assembled with the nozzle in FIG. 2.

In FIG. 4 the mixing chamber 8 of FIG. 3 is illustrated when assembled with a nozzle means 7 as in FIG. 2. From this figure it is readily understood that the fluid flows emerging from the passages 2, 5, respectively, will be disturbed by the fluid perturbation means 11 constituted by the shelves 12, when the apparatus is in use.

Figure 5:
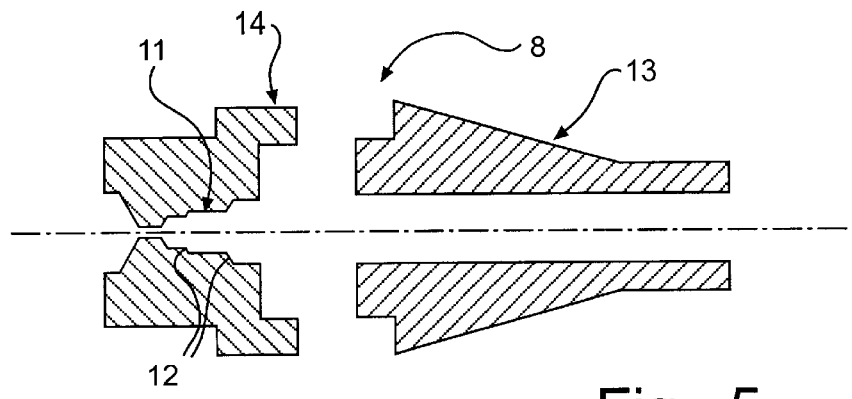
FIG. 5 is a section of another embodiment of a mixing chamber according to the invention, similar to that in FIG. 3, but made in two pieces.

In FIG. 5 a mixing chamber 8 is shown, which is similar to the mixing chamber of FIG. 3, but that is made out of two separate pieces, an inlet end piece 13, and an outlet end piece 14. These two pieces 13, 14 are detachably connectable to one another, and are supposed to be interconnected in use, constituting a functional mixing chamber 8. The possibility of separating the inlet end piece 13 and the outlet end piece 14, provides the advantage of easier cleaning of the mixing chamber 8, in which outlet end particles tend to clog together, sealing the narrow passage to the vessel 6. A further advantage is that outlet end pieces 14 and inlet end pieces 13 having various designs can be easily interchangeable.

Figure 6:
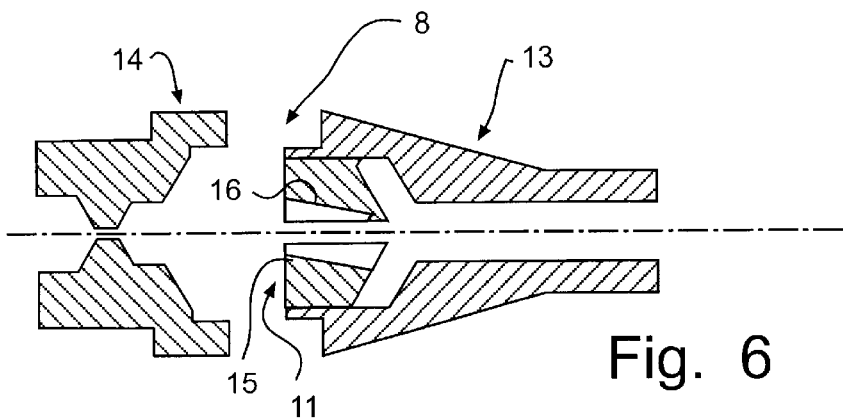
FIG. 6 is a section of a third embodiment of a mixing chamber according to the invention.

Another embodiment of a mixing chamber 8 according to the invention is shown in FIG. 6. It consists of an outlet end piece 14 and an inlet end piece 13, in the same way as the aforementioned embodiment. The flow perturbation means 11 is constituted by a plug 15, which is sealingly introduced in the open end of the outlet end piece 13. The plug 15 is further provided with a central throughout bore 16, which bore 16 provides a passage that is inclined with respect of the central axes of the mixing chamber 8, which is also the direction in which the fluids emerge from the nozzle 7. When in use, the bore 16 will create shear forces, acting on the fluid flow so as to rotate the bypassing fluid and thus create turbulence spreading inside of the mixing chamber 8. The plug 15 provided with the bore 16 thus realizes the flow perturbation means 11 in this particular embodiment.

Figure 7:
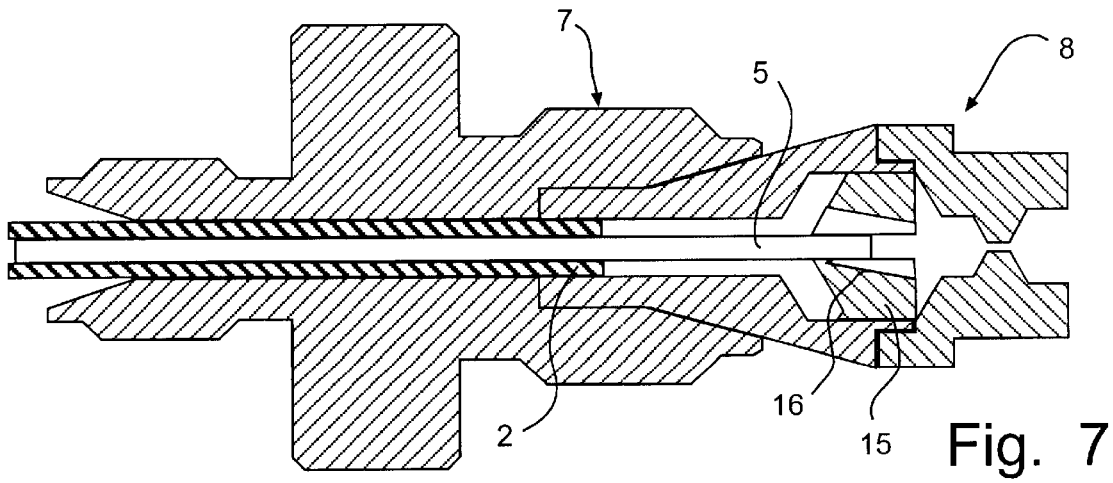
FIG. 7 is a section of the mixing chamber in FIG. 6 in an assembled state together with the nozzle in FIG. 2.

In FIG. 7 the mixing chamber 8 in FIG. 6 is shown in an assembled state with nozzle means 7. With the proportions between parts as in FIG. 7, it is clear that the turbulence in this case will first appear upstream of the opening of the central passage 5, and is then likely to spread inside of the mixing chamber 8.

Figure 8:
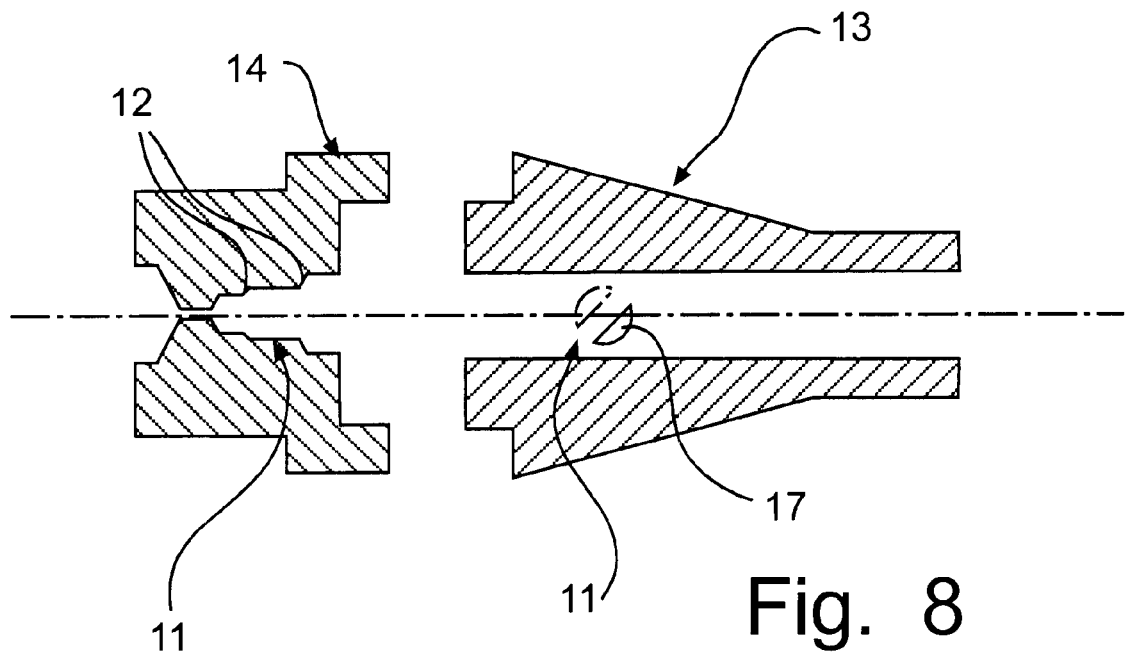
FIG. 8 is a section of a fourth embodiment of a mixing chamber according to the invention.
Figure 8A:
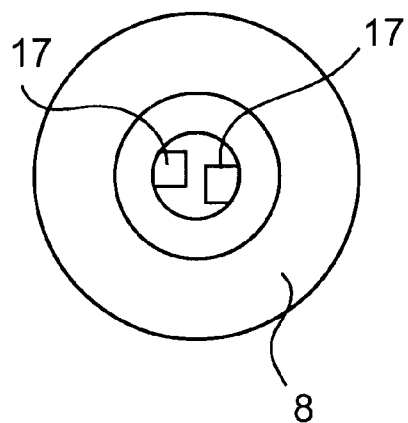
FIG. 8*a* is a longitudinal section of the mixing chamber in FIG. 8.

Yet an other embodiment of a mixing chamber 8 according to the invention is shown in FIG. 8. This mixing chamber 8 has an inlet end piece 13 and an outlet end piece 14. The flow perturbation means 11 is constituted by two separate means. The outlet end piece 14, is provided with two chamfered shelves 12, similar to the shelves in FIG. 2, constituting a first flow perturbation means. The inlet end piece is provided with a second flow perturbation means 11, comprising two baffles 17, extending from the wall of the mixing chamber 8. As seen more clearly from FIG. 8b, the baffles 17 only extend just so far as to let the central passage 5 pass between them. The baffles 17 are further arranged in an angle against the central axes of the mixing chamber 8 in order to increase their effect on the flow.

The effect of the flow perturbation means 11 is clearly seen in the following experiments. In all these experiments, SEDS equipment was used for preparing the particles. The solution and the antisolvent ($CO_2$) were introduced through a nozzle, which was located in an oven. Under controlled pressure and temperature conditions, the antisolvent extracted the solvent from the solution.

Figure 9B:
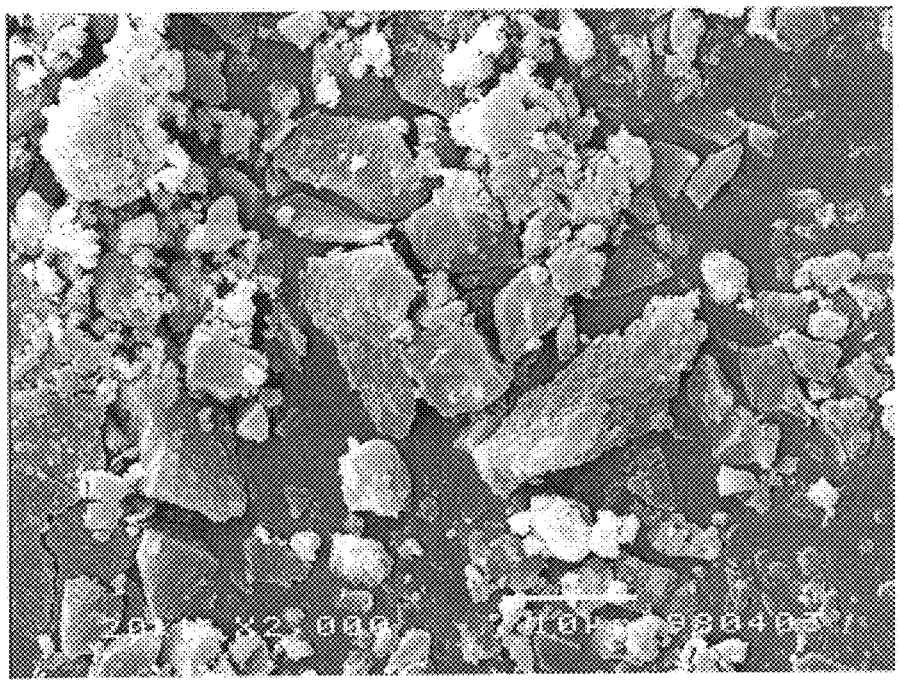
FIG. 9*b* is a SEM-graph from an experiment using the mixing chamber in FIG. 8 and felodipine as the particle forming substance.
Figure 9B:

With the test substance felodipine, which has low molecular weight and is crystalline, the same experiment was made using a mixing chamber according to prior art and a mixing chamber according to the embodiment of the invention shown in FIG. 8. Ethyl acetate was used as solvent and $CO_2$ as anti solvent. The running conditions were 80 bar and 60 degrees C. The flow rate of the antisolvent was 9.0 ml/min. and the flow rate of the solution 0.1 ml/min. The SEM graphs of the particles formed in each experiment was then studied. In FIG. 9a, the SEM graph using prior art technology is shown, and in FIG. 9b, the SEM graph using the mixing chamber of FIG. 8 is shown. It is clearly seen that the mixing chamber according to the invention provides different and preferable particles than the particles formed by prior art. The particles formed by the method according to the invention are visibly smaller and more uniform than the particles obtained by the prior art method.

Figure 10A:
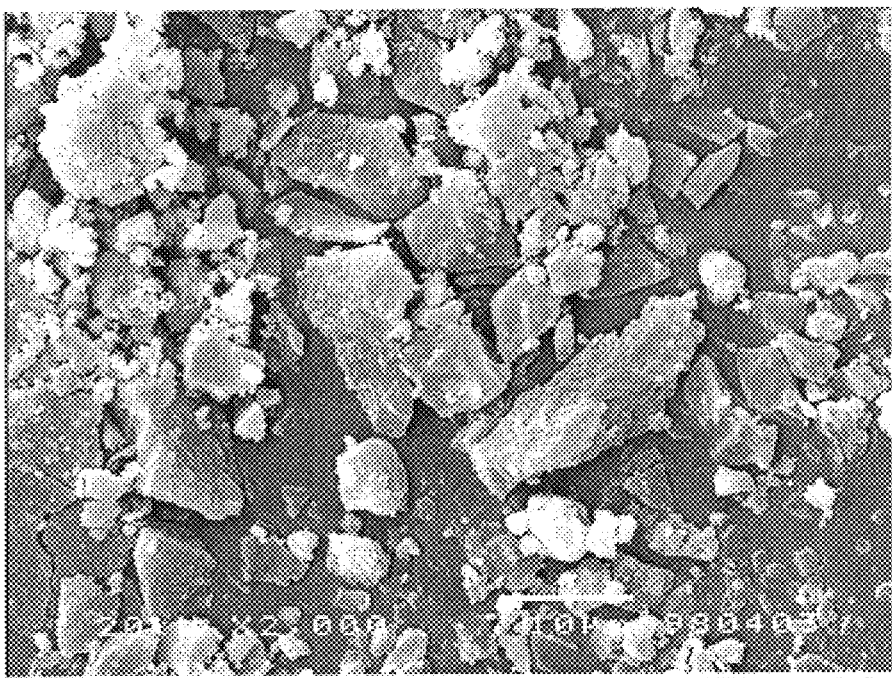
Figure 10B:
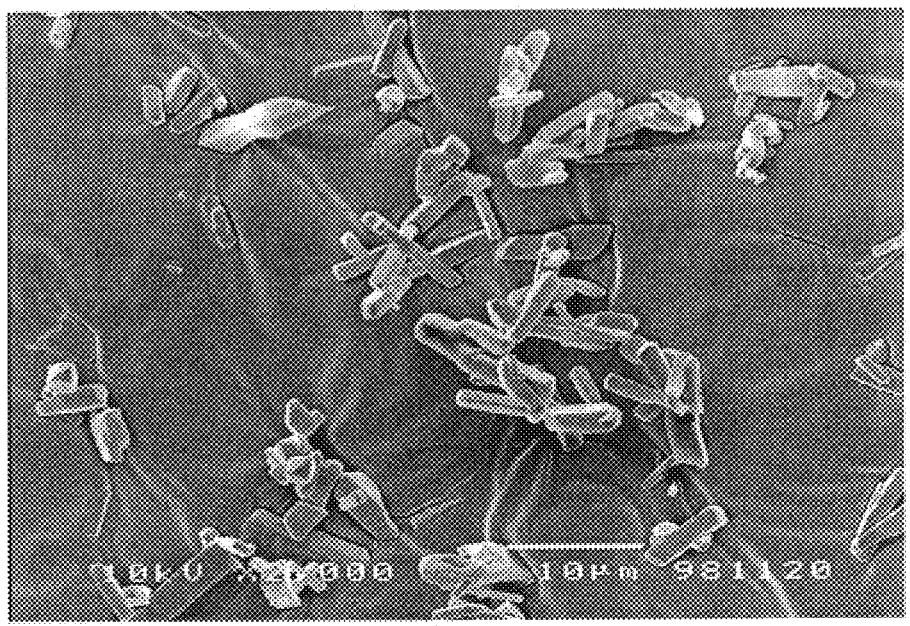
FIG. 10*b* is a SEM-graph from an experiment using the mixing chamber in FIG. 6 and felodipine as the particle forming substance.

A third experiment was made using felodipine and the mixing chamber from FIG. 6. The test conditions were the same as in the first experiment with felodipine. Here, both morphology and size of the particles are clearly different from the experiment using prior art, as seen from the SEM-graphs (FIGS. 10a and b). The morphology obtained by using the mixing chamber from FIG. 6 is highly preferable to the morphology of prior art particles, since the particles are more uniform and considerably smoother.

Figure 13:
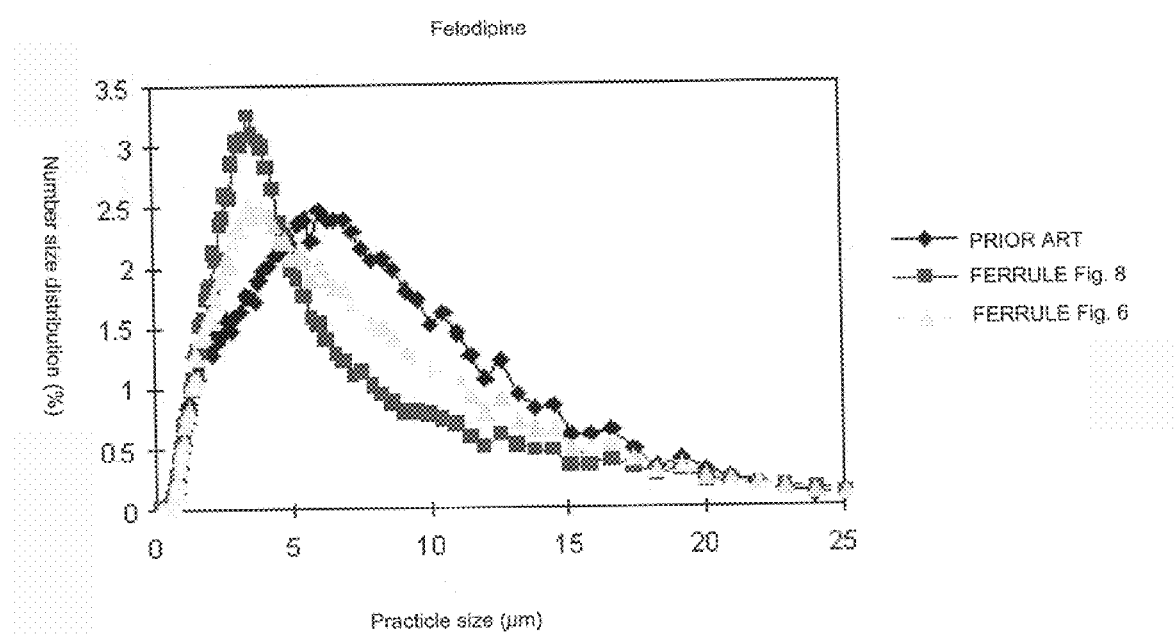
FIG. 13 is a diagram showing the size distribution of particles when using felodipine as the particle forming substance and three different mixing chambers.

The size distributions using felodipine with different mixing chambers are shown in FIG. 13. Both of the mixing chambers according to the invention show a narrower size distribution that is also translated towards smaller particle sizes. As seen, for this particular substance, the mixing chamber according to FIG. 8 shows a better result than the mixing chamber according to FIG. 6. For an optimal result, each substance should be used together with a mixing chamber specifically adapted for that substance and the desired particle formation of said substance.

Figure 11A:
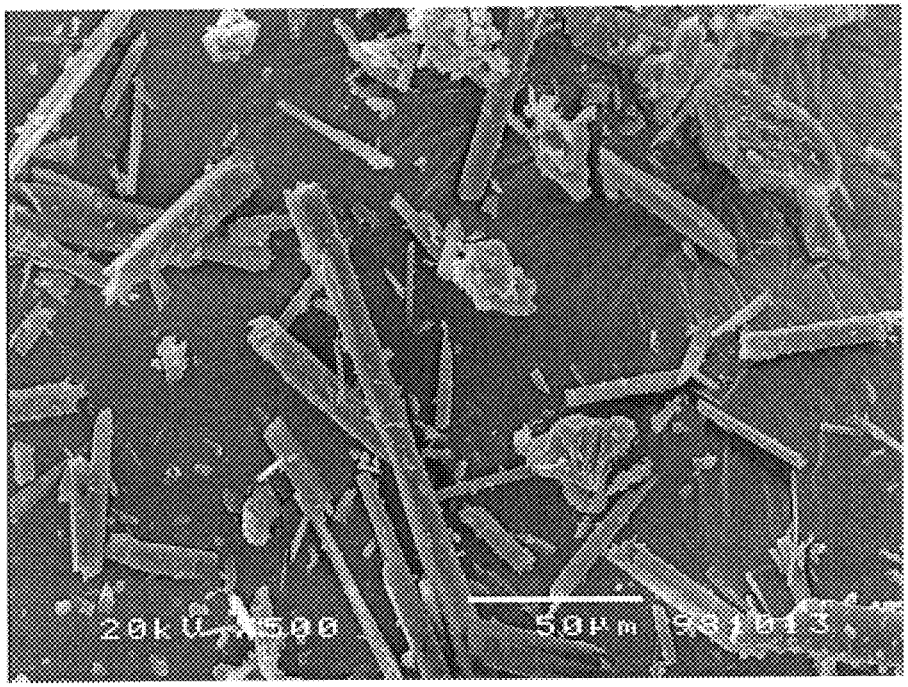
FIG. 11*a* is a SEM-graph from an experiment using a mixing chamber according to prior art and candesartan cilexetil as the particle forming substance.
Figure 11B:
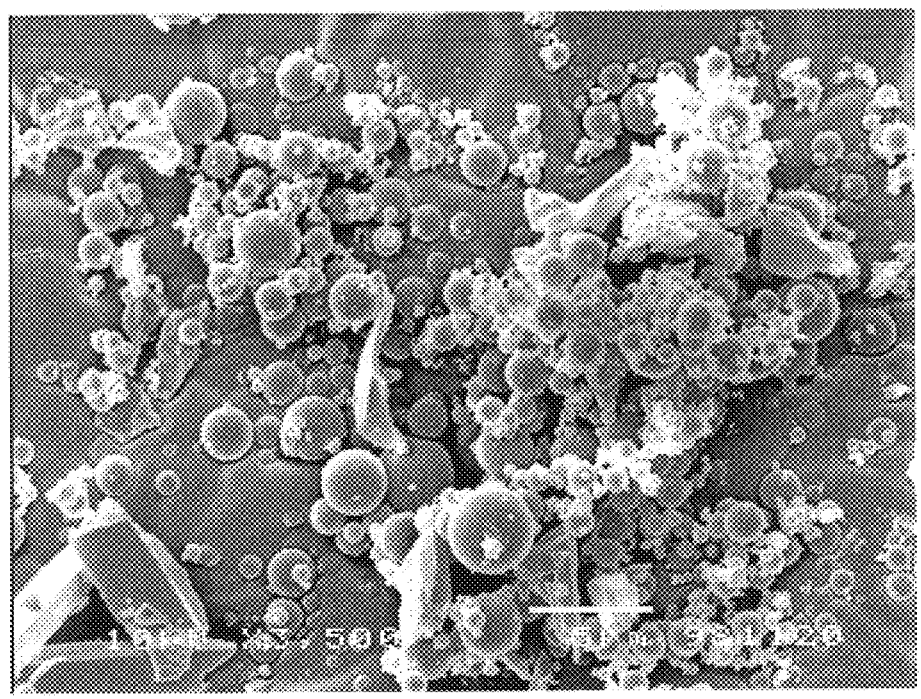
FIG. 11*b* is a SEM-graph from an experiment using the mixing chamber in FIG. 5 and candesartan cilexetil as the particle forming substance.
Figure 12A:
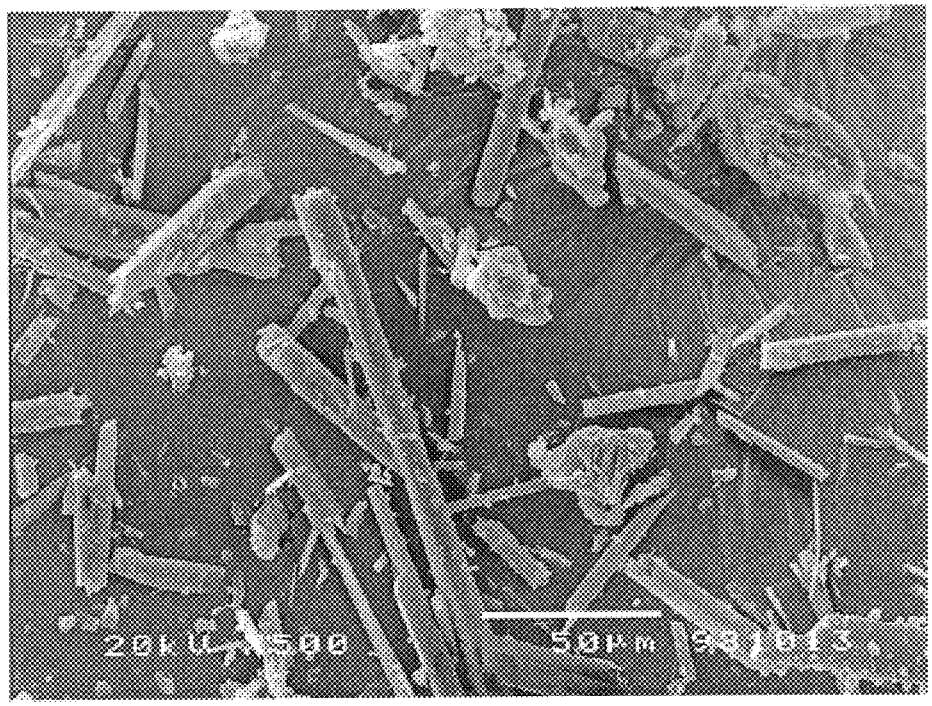
Figure 12B:
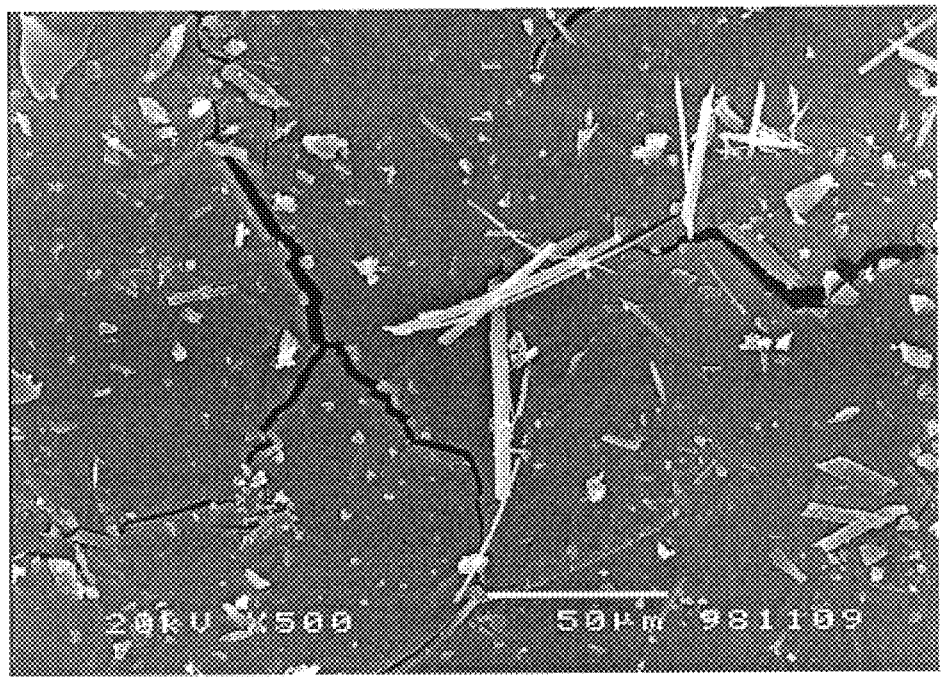
FIG. 12*b* is a SEM-graph from an experiment using the mixing chamber in FIG. 6 and candesartan cilexetil as the particle forming substance.

Another test substance, candesartan cilexetil was used in similar experiments using the mixing chamber from FIG. 5 and FIG. 6. The resulting SEM-graphs are shown in FIGS. 11a and b and 12a and b, respectively. The running conditions in these experiments were 210 bar and 64 degrees C. The flow of the antisolvent ($CO_2$) was 12 ml/min and the flow rate of the solvent (acetone) was 0.3 ml/min. The differences between the resulting particles when using prior art and when using the different embodiments of the mixing chamber according to the invention is remarkable, as clearly seen in the SEM-graphs. Again, the morphology and the size distribution of the particles are advantageously affected by the controlled disorder in the fluid flow or flows.

It will be appreciated that many different embodiments of the method, concerning the creation of the controlled disorder, and in the mixing chamber, concerning the shape and positioning of the fluid perturbation means can be made within the scope of the invention. The fluid perturbation means can for example be shaped like baffles extending from the walls of the mixing chamber, like grooves or protuberances in the mixing chamber wall or be constituted by the insertion of channels in such way to set the fluid inside the mixing chamber in rotation. One could also imagine the turbulence to be created before entering the mixing chamber, in the passages of the nozzle. The outer form of the mixing chamber can evidently have many different shapes adjusted to the shape of the nozzle used.

Different flow perturbation means in the front or the end part of the mixing chamber can be put together as required for forming particles of a certain substance. The length of the passages 2, 5 entering the mixing chamber 8 might have an impact on the creation of turbulence.

It is appreciated that, although the examples shown in this paper are limited to two passages for leading a fluid gas and a vehicle system, the invention can readily be realized is with three or more passages. In such an embodiment, more than one solution can thus simultaneously be used in the method according to the invention.

We claim:

1. A method for forming particles of a substance, comprising the step of introducing into a mixing chamber, in which the temperature and pressure are controlled, a fluid gas and at least one vehicle system comprising at least one substance in solution or suspension such that droplet formation and extraction of the vehicle occur substantially simultaneously by the action of the fluid gas; wherein turbulence is induced in at least one of said fluid gas and said vehicle system to create a controlled disorder in the flow of the at least one of the fluid gas or the vehicle system in order to control the particle formation in said mixing chamber, said controlled disorder being created by at least one flow perturbation means arranged in the interior of the mixing chamber or arranged in at least one of the passageways leading the fluids to the mixing chamber.

2. The method according to claim 1, wherein said turbulence is controlled to form the particles of the substance.

3. The method according to claim 1 or 2, wherein the controlled disorder is created by the fluid interacting with the interior of the mixing chamber.

4. The method according to claim 1 or 2, wherein said controlled disorder in the at least one of said fluid gas and said vehicle system is induced in a region near or adjacent to an outlet orifice of said chamber.

5. The method according to claim 1 or 2, wherein said turbulence or disorder of the at least one of said fluid gas and said vehicle system is caused by the fluid interacting with at least one flow perturbation means arranged in the interior of said mixing chamber.

6. A mixing chamber for forming particles of a substance, said mixing chamber comprising a chamber having an inlet for receiving at least one first supply member having an outlet for supplying a fluid gas and at least one second supply member having an outlet for supplying a vehicle system comprising at least one substance in solution or suspension, and an outlet for exhausting the particles formed therein, wherein at least one flow perturbation means is disposed in the interior of the mixing chamber or is disposed in at least one of the passageways leading the fluids to the chamber for interacting with at least one of the fluid gas or vehicle system supplied by the at least one supply member to induce turbulence in the at least one of the fluid gas or vehicle system for creating a controlled disorder in the flow of the at least one of the fluid gas or the vehicle system in order to control the particle formation in said mixing chamber.

7. The mixing chamber according to claim 6, wherein said flow perturbation means is designed to induce a turbulence that is controlled to form the particles of the substance.

8. The mixing chamber according to claim 6 or 7, wherein said flow perturbation means comprises a flow perturbation element that is disposed within said mixing chamber.

9. The mixing chamber according to claim 8, wherein the flow perturbation element is formed in the contour of the inner walls of the chamber.

10. The mixing chamber according to claim 8, wherein the flow perturbation element comprises a projecting member in the interior of the chamber.

11. The mixing chamber according to claim 8, wherein said flow perturbation element comprises at least one shelf in the wall of the mixing chamber.

12. The mixing chamber according to claim 8, wherein the flow perturbation element comprises at least one baffle extending from said mixing chamber wall.

13. The mixing chamber according to claim 6 or 7, wherein the flow perturbation means is disposed to induce turbulence in at least one of said fluid gas and said vehicle system, in a region near or adjacent to said outlet part of said mixing chamber.

14. The mixing chamber according to claim 8, wherein said flow perturbation means comprises a plug being disposed in the mixing chamber, said plug being provided with a channel.

15. The mixing chamber according to claim 14, wherein the direction of the channel in said plug is inclined with respect to the direction of the fluid flows in the mixing chamber.

16. The mixing chamber according to claim 12, wherein said flow perturbation element comprises two baffles, extending from opposite walls of the mixing chamber.

17. The mixing chamber according to claim 12 or 16, wherein said baffle is inclined with respect to the central axes of the mixing chamber.

18. The mixing chamber according to claim 6 or 7, wherein the mixing chamber comprises first and second body parts, which are coupled to each other and are detachable.

19. An apparatus for producing particulate products, comprising a vehicle system supply, a fluid gas supply, a mixing chamber according to claim 6, a first passage and a second passage for the co-introduction of a vehicle system and a fluid gas into the mixing chamber.

* * * * *

UNITED STATES PATENT AND TRADEMARK OFFICE
CERTIFICATE OF CORRECTION

PATENT NO.     : 6,551,532 B1
DATED          : April 22, 2003
INVENTOR(S)    : Boissier et al.

It is certified that error appears in the above-identified patent and that said Letters Patent is hereby corrected as shown below:

<u>Column 8, line 65 and Column 9, line 14,</u>
Insert "mixing" before -- chamber -- (two instances).

Signed and Sealed this

Second Day of September, 2003

JAMES E. ROGAN
*Director of the United States Patent and Trademark Office*